(12) United States Patent
Albagli (10) Patent No.: US 6,418,193 B1
(45) Date of Patent: Jul. 9, 2002

(54) IMAGING SYSTEM INCLUDING RADIATION FILTER FOR X-RAY IMAGING

(75) Inventor: Douglas Albagli, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/431,412

(22) Filed: Nov. 1, 1999

(51) Int. Cl.[7] .................................................. G21K 3/00
(52) U.S. Cl. ........................................ 378/158; 378/156
(58) Field of Search ................................. 378/156–159

(56) References Cited

U.S. PATENT DOCUMENTS

| | | | |
|---|---|---|---|
| 4,499,591 A | | 2/1985 | Hartwell |
| 4,956,859 A | * | 9/1990 | Lanza et al. ................. 378/157 |
| 5,033,075 A | | 7/1991 | DeMone et al. |
| 5,204,888 A | * | 4/1993 | Tamegai et al. ............. 378/156 |
| 5,285,489 A | * | 2/1994 | Ohtsuchi et al. ............ 378/156 |

* cited by examiner

*Primary Examiner*—Craig E. Church
(74) *Attorney, Agent, or Firm*—Donald S. Ingraham; Christian G. Cabou (57) ABSTRACT

An imaging system including a radiation spectral filter is provided for improving the quality of images obtained without increasing the dosage of radiation to the patient, and a method for improving image quality using such filtering are provided. The radiation filter is made of a material of a high atomic number, in order to filter out low energy and high energy x-rays from the beam of radiation prior to the beam being passed through the object to be imaged.

7 Claims, 9 Drawing Sheets

Fig. 11

IMAGING SYSTEM INCLUDING RADIATION FILTER FOR X-RAY IMAGING

BACKGROUND OF THE INVENTION

This invention relates to an x-ray imaging system which includes a device for filtering x-rays, and, more particularly, to a system employing a spectral filter for filtering x-rays emanating from the exit port of an x-ray tube used in imaging systems.

The filtering of x-rays, or x-ray filtration, is a step that has been employed in x-ray systems, for example, in medical imaging systems, in an effort to improve the images obtained. Materials employed in constructing x-ray spectral filters have included aluminum and copper, and, for low energy applications such as mammography, filters made of rhodium and molybdenum have been used. The material used and the thickness of the filter influence the ability of a filter to absorb x-rays. The spectral filtering by such x-ray filters is performed in order to improve the quality of the image obtained. The filtering of the x-rays to improve image quality has heretofore focused substantially exclusively on blocking low energy x-rays from reaching the patient, and/or from reaching the detector.

The principal goal in using x-ray spectral filtering is to aid in improving the image obtained by the imager, without adversely affecting the object undergoing imaging. Various aspects of an overall imaging system can affect the image quality. The problem to be solved by the present invention is to improve, through the use of spectral filtering of the x-ray tube, the quality of an image obtained in an imaging process, while reducing the dosage or exposure of x-rays to the patient.

BRIEF SUMMARY OF THE INVENTION

An x-ray imaging system is provided having an x-ray source, an x-ray detector, and at least one spectral radiation filter, the spectral radiation filter being disposed between the source and the object to be imaged.

DETAILED DESCRIPTION OF THE INVENTION

The invention is directed to a spectral radiation filter for which the selection of an appropriate material of construction, and of an appropriate thickness, are made such that the spectral filter will filter out portions of the x-ray spectra that do not effectively contribute to producing a high-quality image. As used herein, the "spectral radiation filter" refers to a filter as described herein that provides attenuation of radiation in selected energy ranges to increase the signal level (CF) or alternatively the contrast-to-noise ratio (CNR) at the x-ray detector in the imaging system, or alternatively a combination thereof. In medical imaging systems, the sought-after spectral filtering must also take into account that the dose of x-rays to which the patient is exposed is preferably minimized.

The invention is based upon the determination that, within the spectrum of x-ray energies emitted by the x-ray source and detected by the x-ray detector, certain x-ray energies are more advantageous than others in achieving the higher signal levels and contrast-to-noise ratios, and that by attenuating the less useful x-ray energies, an improved image is obtained and the patient dosage or exposure is kept to a minimum. In an exemplary embodiment of the invention, the x-ray spectral filter is constructed of a material having a high atomic number (Z), e.g., Z=58 or higher when the x-ray spectra exiting the exit port of the x-ray tube is in the range of 50–160 Kvp, typical of high energy medical imaging. In one embodiment, a thickness of the spectral filter would be in the range of between about 40 $\mu$m and about 300 $\mu$m, and the filter is made of material having Z>64.

A spectral filter made of a high-Z material in the prescribed range of thickness can effectively filter out x-rays in spectral ranges determined, in the course of developing the present invention, to be poor contributors to a high-quality image. The use of such a spectral filter results in improvement in the contrast-to-noise ratio (CNR) and an increase in the signal level (CF), for a given unit of exposure to radiation. Thus, a high quality image can be obtained while actually reducing the dose of radiation given to the patient.

Figure 1:
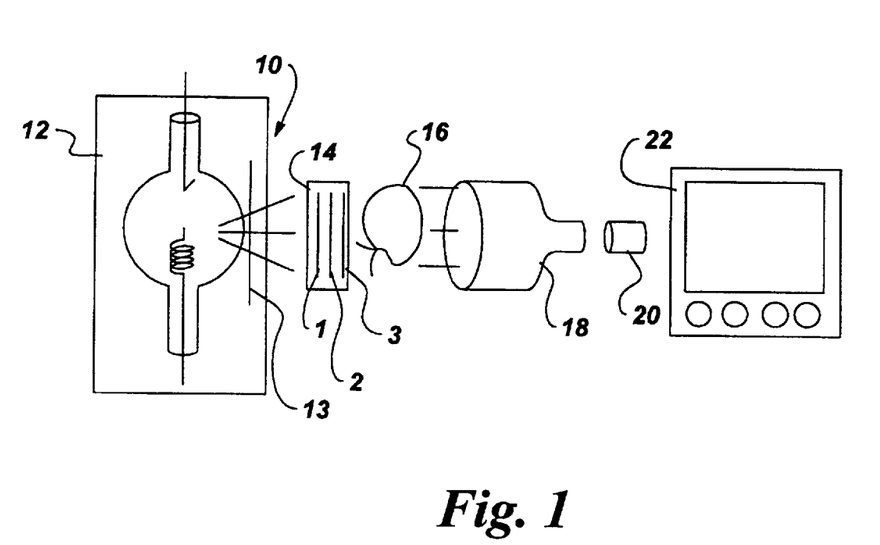
FIG. 1 is a substantially schematic view of an x-ray imaging system with which the spectral filter of the present invention is preferably employed.

FIG. 1 illustrates, in substantially schematic form, an x-ray imaging system, generally designated by the numeral 10, for use in examining the condition of an internal structure of an object 16. The object 16 may be, for example, a human patient in a medical diagnosis procedure. The radiation source 12 is preferably an x-ray tube 12 or generator, with the x-ray spectra commonly used in high energy medical imaging being in the range of 50–160 kVp. This range is sometimes narrowed to about 80 kVp to 120 kVp. A spectral radiation filter 14 is positioned between the exit port of x-ray tube 12 and the object 16 to be imaged. The filter is preferably placed in proximity e.g. in a range between about 0" and 8" from the exit port of the x-ray tube 12 in order to permit the filter to be constructed in as small a size to intercept substantially all x-ray (e.g. 90% or more) emanating from an exit window of the x-ray tube but having an area that does not present significant issues of increased cost or restructuring of the x-ray apparatus. Additionally, placement of the filter in proximity to the x-ray tube to reduce effects of scatter from these filters in the x-ray image. In one embodiment of the invention, the filter 14 has a surface area of about one square inch (1.0 in², that is, about 6.5 cm²). Spectral radiation filter 14 comprises at least a primary filter material layer 1 of an x-ray a first attenuating material (e.g., preferably fabricated of a thin layer, such as a sheet or foil, of a metallic material), and in alternative embodiments described below, may comprise a plurality of layers of filter material, e.g., secondary filter material layer 2 and a tertiary filter material layer 3, as shown in FIG. 1.

In some x-ray systems, the system 10 also includes a pre-filter 13 disposed as an integral part of x-ray tube assembly 12. This pre-filter, when employed, typically comprises a low Z material (e.g., Beryllium (Z=3)) and performs an initial filtering of the low energy x-rays.

The filter 14 is provided to obstruct or attenuate x-rays of certain energy levels that have been determined to be harmful to, or to not contribute significantly to, a higher quality image of the object under examination. The filtered radiation beam passes through the object 16, and may preferably be received by a radiation detector 18 such as an image intensifier or solid state radiation detector. The radiation detector produces an output signal that is further processed to produce the desired image for use by the operator. In one embodiment, the output is processed by an image processor 20 to produce an electronic signal that may be displayed on a video monitor 22.

In the course of developing the x-ray imager system 10 of the present invention, spectral filtering of the x-ray exiting the x-ray generator was identified as an aspect of the system that could be changed or modified to improve the performance of the imager. Improved performance can be evidenced by an increase in the signal level on the imager, which increase tends to reduce the effect of electronic noise. In light of the fact that a principal envisioned use of the x-ray imager is to analyze the condition of human patients, any increase in signal level desirably will not come at the expense of increasing the radiation exposure to the patient.

The approach for achieving the desired result noted above is to design a spectral filter, based upon the recognition that certain x-ray energies within the complete spectrum of x-ray energies generated by an x-ray source contribute, to a greater extent than other x-ray energies, to improved imaging capabilities. The spectral filter will thus desirably filter out the x-rays of less-than-optimal energies (in terms of contribution to quality imaging), while allowing the x-rays at the more optimal energies to pass through to the scintillator. In one embodiment of the invention, this goal is achieved by constructing a spectral filter from a material having a high atomic number (Z) (as used herein, "high atomic number" refers to a material having a Z value of at least 58), and desirably an atomic number of Z≧65.

Figure 2:
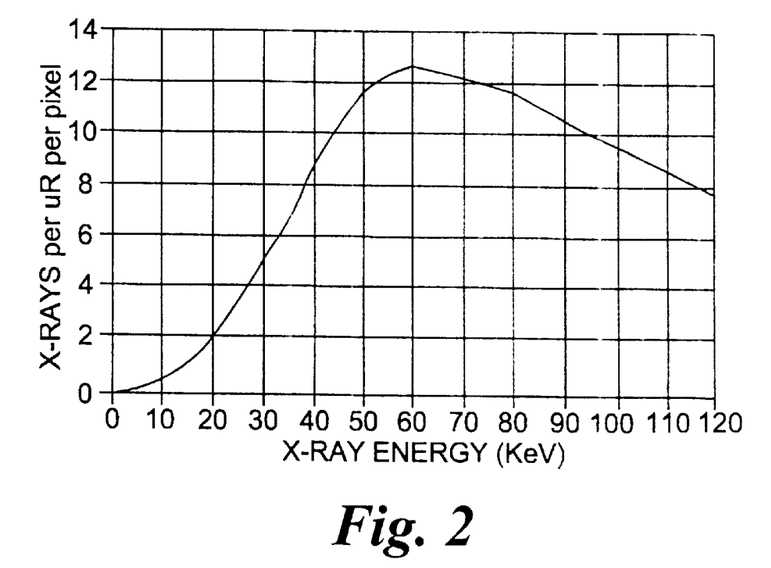
FIG. 2 is a graph illustrating the number of x-rays of a range of x-ray energies needed to produce an exposure of 1 $\mu$R.
Figure 3:
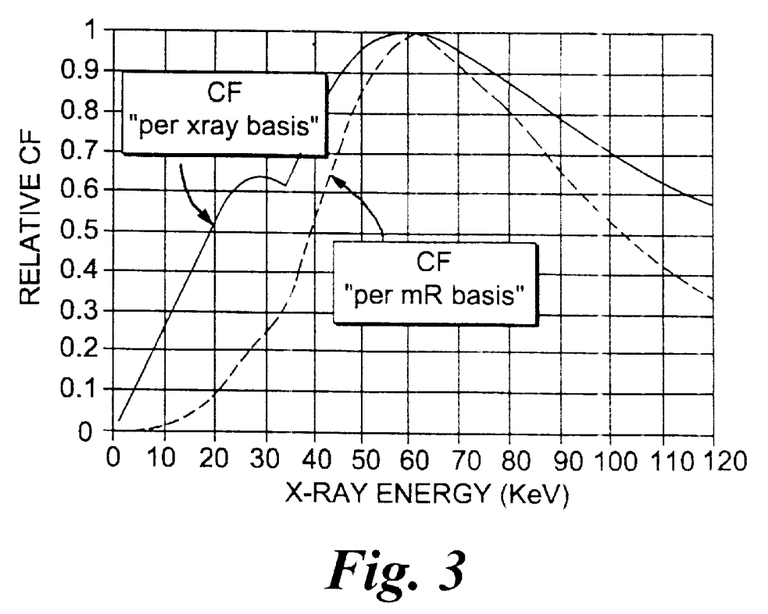
FIG. 3 is a graph plotting relative conversion factors as a function of x-ray energy for a digital imager in accordance with the present invention.

FIG. 2 presents a graph which illustrates the number of x-rays at various given energies that are needed to generate an exposure of 1.0 µR (micro-Roentgen). This graph establishes the relationship between x-ray flux and exposure of the patient to radiation. FIG. 3 presents a plot of a relative "conversion factor" of the x-rays as a function of x-ray energy. The "conversion factor" is the signal level produced in a given image detector by a single x-ray for a particular detector (for purposes of this example, a solid state imaging device). The solid line plotted is a measure of the relative conversion factor presented in terms of units of electrons per incident x-ray when a CsI scintillator (420 µm thick) is employed. Also plotted on the same graph, in a broken line, is the relative conversion factor plotted as a function of energy per milli-Roentgen (mR) to the patient.

The gap between the solid line and the broken line in FIG. 3 provides an indication of the relative effectiveness of x-rays of the particular energies displayed on the graph at delivering a percentage of the conversion factor (related to signal level in the detector), on a "per x-ray" basis (solid line), and on a "per exposure dosage" (mR) basis (broken line). Thus, initially, it is seen from FIG. 3 that x-rays having energies from about 40 KeV to about 95 KeV will have the effect of maximizing the signal level in the detector, with respect to patient dose or exposure, in that the values of the conversion factor (CF) on the "per exposure dosage" basis lie close to the conversion factor values on a "per x-ray" basis. In contrast, for example, it can be seen that, while x-rays having an energy of 27 KeV deliver about 60% of the conversion factor of a 60 KeV x-ray on a "per x-ray" basis, those x-rays deliver only about 20% of the conversion factor of a 60 KeV x-ray, on a "per exposure dosage" (mR) basis.

The ability to see an object of interest in an image is related to the contrast between the object and the noise in the image. Thus, in addition to seeking to obtain increased signal levels at constant or decreased dosages, the contrast produced in a given image and more significantly, the contrast-to-noise ratio, should be maintained as high as is practicable.

For the purposes of the development of this invention, a relative contrast-to-noise ratio (rCNR) value was obtained through normalizing a contrast-to-noise ratio of a detector using the CsI scintillator, against an ideal detector. This value provides a figure of merit for comparing the effects of different x-ray spectra, and is preferably expressed as:

$$rCNR = C \cdot S_N = C \cdot \sqrt{X_{TB} \cdot QDE} \; ; \qquad (1)$$

where C is a value of contrast determined by a background signal level and a signal level of the combined background and the object undergoing imaging, and $S_N$ (signal to noise ratio), is the square root of the number of absorbed x-rays. Equation (1) indicates that the number of absorbed x-rays is equal to the product of an incident x-ray flux ($X_{TB}$) on the detector, and the fractional absorption (QDE) of the scintillator which, in this preferred embodiment, is made of CsI.

In order to determine which x-ray energies in the x-ray spectrum produce the best relative contrast-to-noise ratios (rCNR), simulations were conducted with four (4) different objects against three different backgrounds. The objects employed were steel guide wire, iodine contrast fluid, bone, and soft tissue (represented by the curve in the Figure marked "density change" as this curve was represented by LUCITE® (generically known as polymethylmethacrylate, or PMMA) material representative of soft tissues of slightly different densities). The backgrounds, chosen to simulate thin, normal, and heavy patients (as these terms are commonly used in the imaging arts), were LUCITE® panels of 20 cm, 25 cm and 30 cm thickness, respectively. LUCITE® is a registered trademark of ICI Acrylics, Inc., of Wilmington, Mo. In this simulation, the thicknesses of the four objects were adjusted to provide contrasts of 5% for the bone and soft tissue, and 10% for the steel and the iodine.

Figure 4:
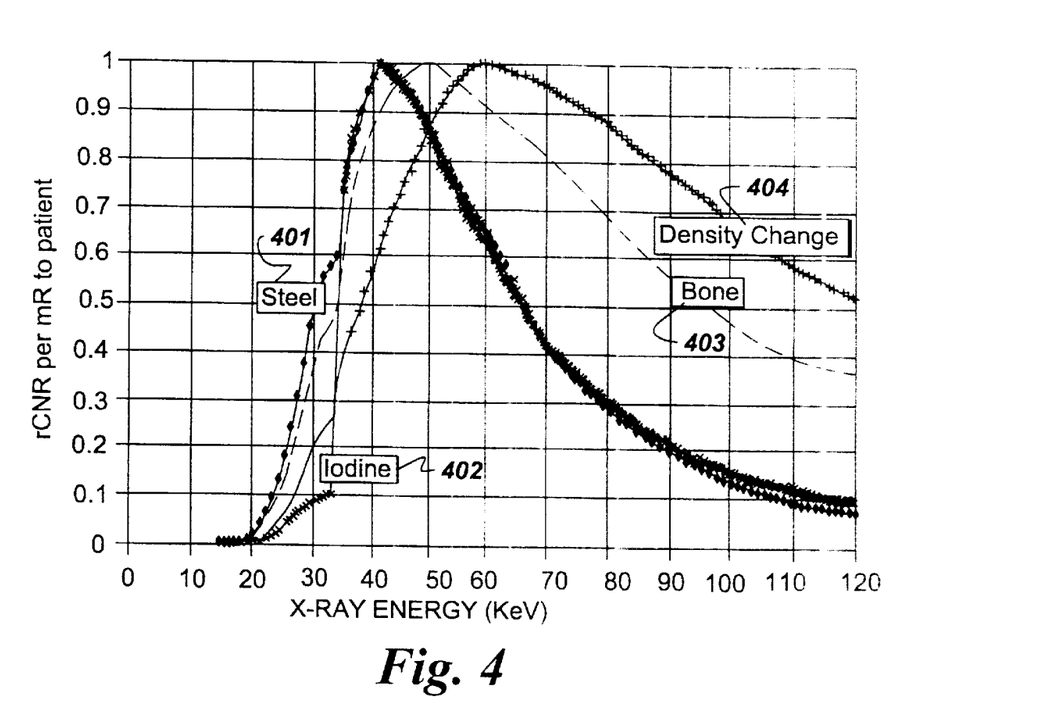
FIG. 4 is a graph illustrating the relative contrast-to-noise ratio as a function of x-ray energy for the different simulations conducted for a digital imager in accordance with the present invention.
Figure 5:
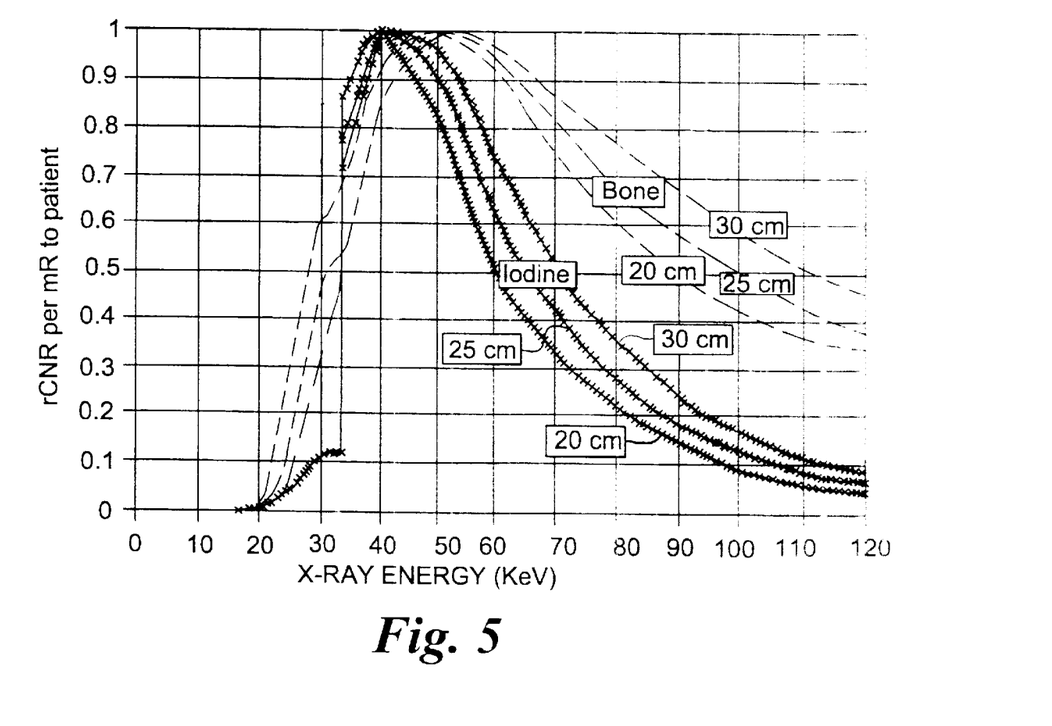
FIG. 5 is a graph illustrating the variation in relative contrast-to-noise ratio as a function of x-ray energy, resulting from changing the background of the image.

FIG. 4 illustrates the relative contrast-to-noise ratio (rCNR) as a function of x-ray energy, for the four objects, using the 25 cm background panel. In this simulation, the x-ray flux at each energy level was adjusted so as to give the same incident exposure to the patient. The results presented in FIG. 4 thus represent a comparison of rCNR on a "per exposure dosage" (per mR) basis. FIG. 5 illustrates the effect of the background thickness (simulating lighter to heavier patients) on the results.

At low x-ray energies, the rCNR is low because fewer incident x-rays reach the object being imaged, and because there are fewer x-rays transmitted through the patient due to absorption. The rCNR is also seen to be low at the higher energies, as the contrast between object and background decreases with the use of higher x-ray energies.

The data presented in FIGS. 3–5 lead to the conclusion that maximization of the signal level and minimization of patient exposure is achieved preferably with a monoenergetic beam of about 60 KeV x-rays. In addition, as seen in FIGS. 4 and 5, the contrast-to-noise ratio, on a "per exposure dosage" basis, can be maximized by use of x-rays having energies in the range of 40–60 KeV. More specifically, for the simulation objects, the rCNR is maximized for the steel and iodine objects at an x-ray energy of about 40 KeV, at about 50 KeV for bone and at about 60 KeV for the imaging of tissue density changes.

Using such simulations, a specific x-ray energy can, in many cases, be identified as the optimal energy for use with a specific object and a specific background. In actual medical imaging, however, it would be impossible, as a practical matter, to provide an imager having the capability of delivering the precise x-ray energy for each different patient and for each different region of interest on each patient. Accordingly, in one embodiment of the present invention, a range of useful or especially advantageous x-ray energies is segregated from x-ray energies which detract from, or do not significantly contribute to, higher signal levels and higher rCNRs in the imaging process.

Figure 6:
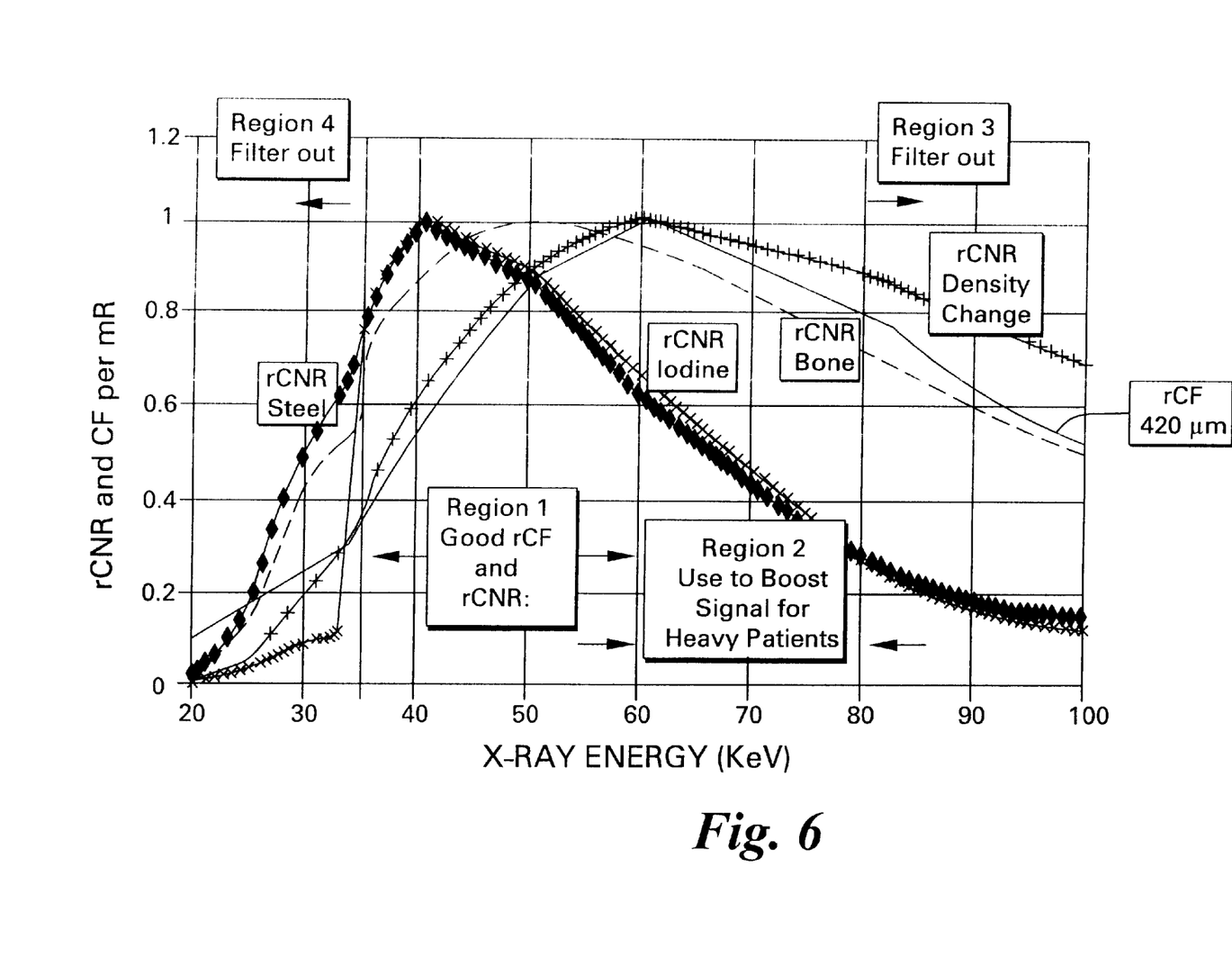
FIG. 6 is a graph illustrating relative contrast-to-noise ratios and conversion factors per unit of exposure as a function of x-ray energy, divided into regions which contribute effectively to obtaining high quality images, and regions which do not contribute effectively.

In FIG. 6, the spectrum of energies from 20 KeV to 100 KeV is shown divided into four different regions. Region 1, which includes x-ray energies from 35 to 60 KeV, is selected as being the ideal range of x-ray energies for maximizing rCNR and signal level, while maintaining patient exposure at a reasonable level. A second region, designated as Region 2, with x-ray energies in the range of 60–80 KeV, is seen as providing a good rCNR for a bone specimen and for tissue density fluctuations, and provides a maximum signal level for these objects. In accordance with a preferred embodiment of the present invention, this energy region is seen as being useful especially for heavier patients, due to x-ray tube power limitations.

It was determined in developing the present invention that the regions designated as Regions 3 and 4 (above 80 KeV and below 35 KeV, respectively) do not benefit the quality of the image obtained, and that filtering out these x-ray energies will thus enhance the quality of the image obtained. The high x-ray energies of Region 3 (a "high end" of a spectrum of x-rays emitted by the source) provide lower rCNR and signal levels (relative conversion factor, or rCF), and thus are preferably filtered out. The low x-ray energies of Region 4 (the "low end" of a spectrum of x-rays emitted by the source) contribute very little to rCNR and rCF, while they greatly increase exposure of the patient to the radiation. The Region 4 x-rays are thus also preferably filtered out.

Figure 7:
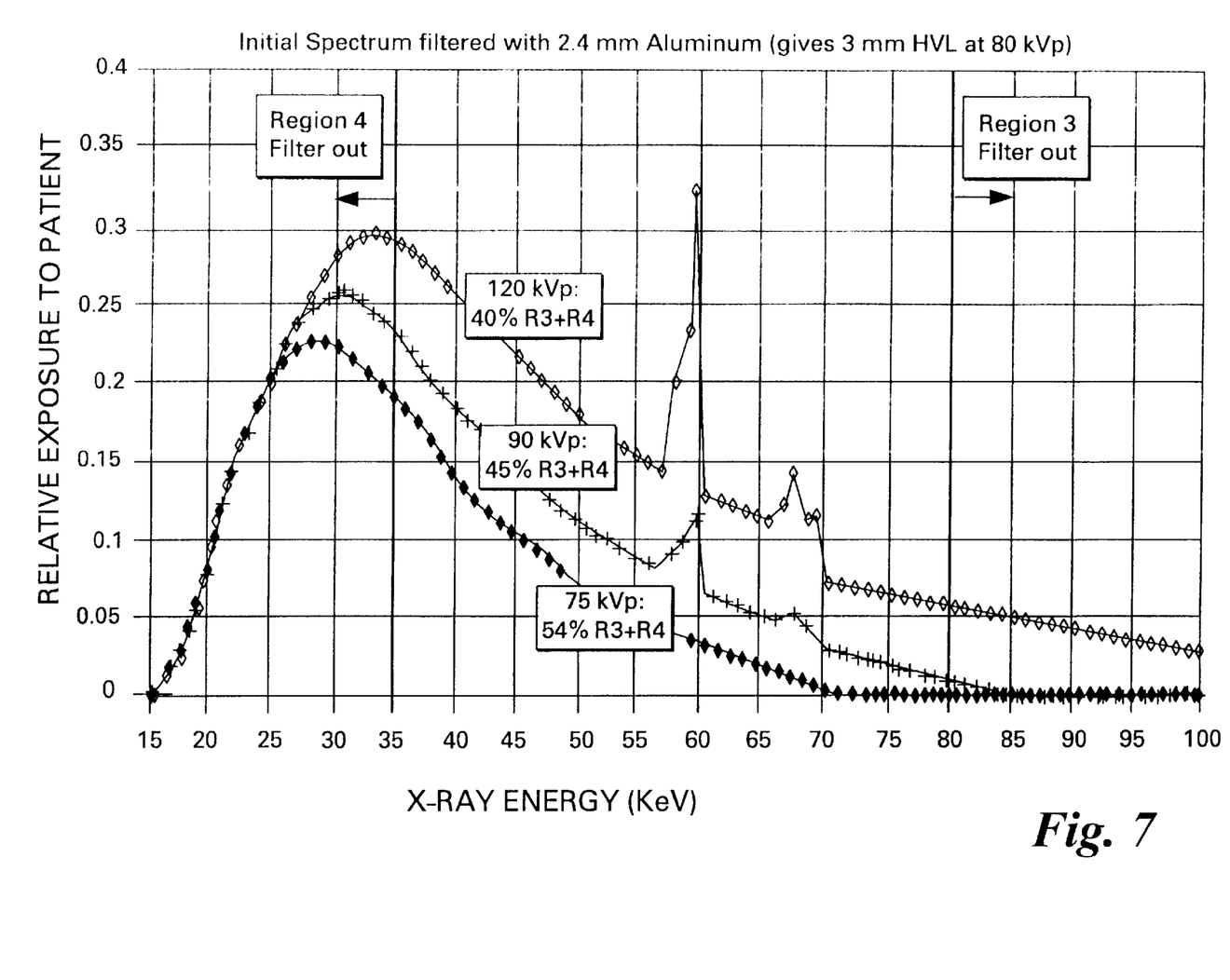
FIG. 7 is a graph illustrating the x-ray spectrum of energies irradiating an object to be imaged using a 2.4 mm aluminum filter, with three different x-ray power levels.

FIG. 7 presents an illustration of a typical x-ray spectrum for a typical imaging system currently in use, which employs an aluminum filter (2.4 mm thick) as an initial filtering medium. The graph shows the same regions of grouped x-ray energies as were developed and illustrated in FIG. 6. It can be seen in FIG. 7 that, despite the use of an initial filtering medium, between 40% and 54% of the x-ray exposure to the patient is from x-ray energies in the regions identified as Regions 3 and 4, the two regions determined to adversely affect, or to be poor contributors to, the quality of the image. The three separate curves in FIG. 7 represent the exposures at three different kVp levels (75 kVp, 90 kVp, 120 kVp) that would commonly be used, for patients of various sizes or builds.

The approach used in the present invention for narrowing the x-ray spectrum to the desired Region 1 and Region 2 energies, nominally from about 35 keV to about 80 keV (see FIG. 6), is to provide a spectral filter made of one of a group of specially selected materials. Also, in order to accommodate the broadest range of patient sizes with a manageable number of filters, the thicknesses of the filters are selected to optimize the filtering within practical limits.

The x-ray attenuation of a filter is a function of the incident x-ray energy, the thickness of the filter, its density, and the elemental composition of the filter. Prior filtering of incident x-rays focused exclusively on attempting to filter out low energy x-rays, such as those designated in Region 4 in FIG. 6. The behavior of different prospective filter materials for filtering these low x-ray energies has, in the development of the present invention, been determined to be dependent upon filter thickness, and, by varying the thickness of filters of the different materials, the respective x-ray attenuation values of the filters can be matched. This can be seen in FIG. 8, which illustrates the x-ray attenuation of filters made of aluminum (Z=13; 6500 µm thick), copper (Z=29; 196 µm thick), molybdenum (Z=42; 67.7 µm thick) terbium (Z=65; 150 µm thick), tungsten (Z=74; 43.9 µm thick), and lead (Z=82; 56.4 µm thick).

Figure 8:
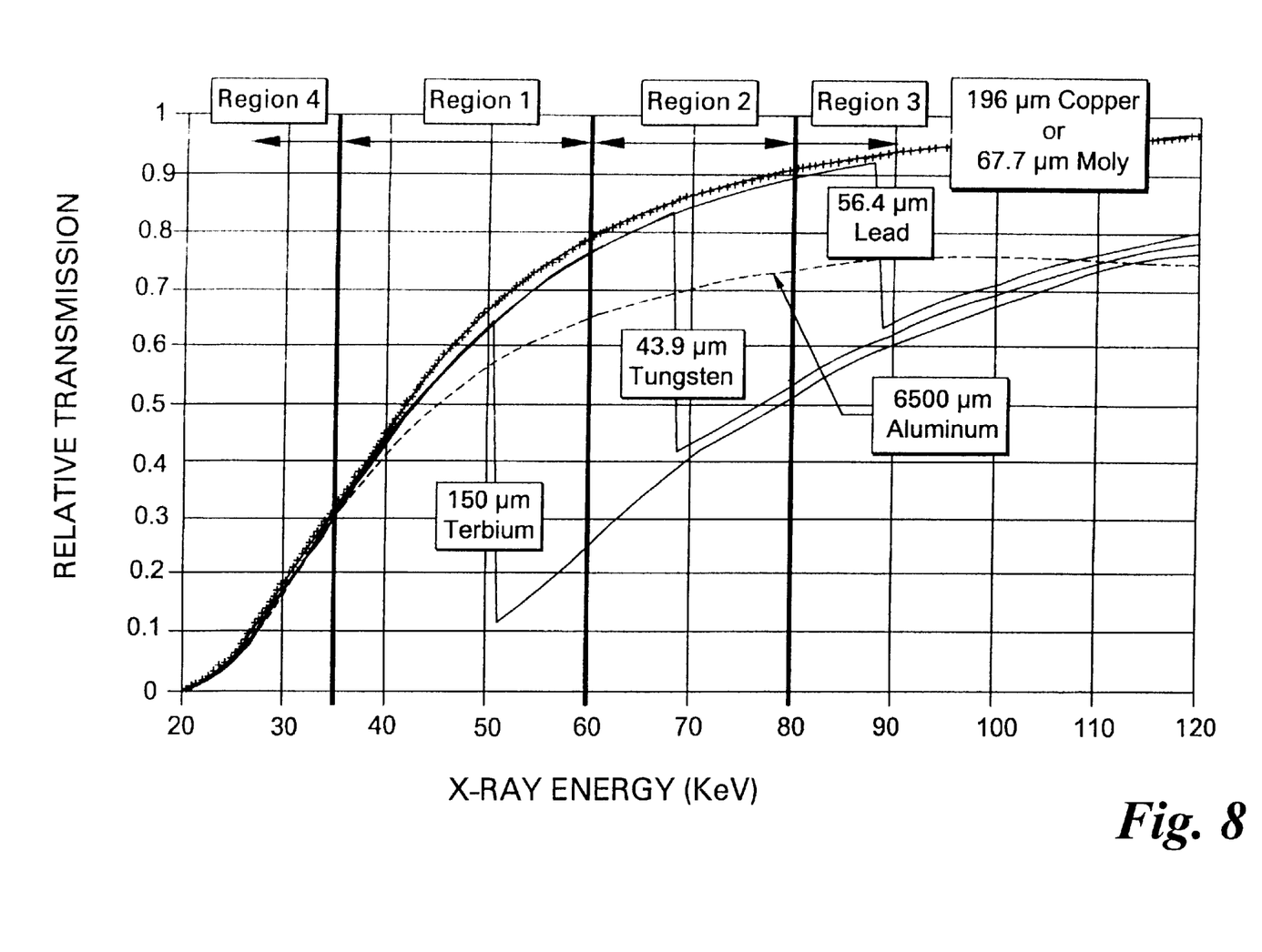
FIG. 8 is a graph illustrating relative x-ray transmission through filters made of different materials and/or of different thicknesses.

It was determined, in the course of developing the filters of the present invention, that the behavior of the materials at the high end of x-ray energies which are desired to be filtered or attenuated, makes a greater difference in terms of which materials will provide the optimal combination of filtering both the low energy (Region 4) x-rays and the high energy (Region 3) x-rays. Specifically, high atomic number (Z≧58), and, especially even higher (Z>64) materials were discovered to behave in such optimal fashion. This behavior is due not to the commonly looked-to factors of the thickness and density of the filter, nor the incident x-ray energy, but is instead due to desirable quantum mechanical effects experienced in the high atomic number materials in which increases in x-ray absorption are discontinuous at a few well-defined energies.

It can be seen in FIG. 8 that aluminum, which has previously been employed in initially filtering x-rays from an x-ray source, has a relatively weak preferential treatment for x-rays in Region 1 (desirable) versus Region 4 (undesirable). The relative flattening of the curve for the aluminum filter is due to the effects of Compton scattering, which takes place in higher Z materials only at higher energies. Copper is seen in FIG. 8 as providing a greater preferential treatment of x-rays in Regions 1 and 4.

Significantly, however, FIG. 8 illustrates that the higher atomic number materials exhibit a discontinuous drop in x-ray transmission (increase in attenuation) at material-specific energies, which leads to increased attenuation in Region 3, as compared with copper or molybdenum. Thus, these materials provide the ability to attain an acceptable relative attenuation of Region 4 x-rays to Region 1 x-rays, and also preferentially attenuate Region 3, and, to an extent, Region 2.

The discontinuous increase in absorption experienced with the high Z materials is due to the quantized nature of the electronic orbitals, and the well-defined energies correspond to the L and K shells of the atom of the particular element. K-edge effects can be seen in FIG. 8 for terbium (K-edge=52 KeV), tungsten (K-edge=69.5 KeV) and lead (K-edge=88 KeV). Table I below details the K-edge energies for several high-Z materials of interest, as well as their potential optimal uses.

TABLE I

| Element | Z | K-edge | Patient | Note |
|---|---|---|---|---|
| terbium (Tb) | 65 | 52.0 | Thin/Med | Boost Contrast for Steel/Iodine |
| thulium (Tm) | 69 | 59.4 | All | Good Compromise |
| lutetium (Lu) | 71 | 63.3 | All | Good Compromise |
| tantalum (Ta) | 73 | 67.4 | Med./Heavy | |
| tungsten (W) | 74 | 69.5 | Med./Heavy | |
| gold (AU) | 79 | 80.7 | Heavy | Boost Signal |
| lead (Pb) | 82 | 88.0 | Heavy | Boost Signal |
| bismuth (Bi) | 83 | 90.5 | Heavy | Boost Signal |

Based solely on the consideration of the desire to deliver the entire x-ray spectrum of Region 1 (FIG. 6, 35–60 KeV), the ideal filter would be made of thulium (Z=69), a rare earth metal having a K-edge at 59.4 KeV. The use of thulium or a higher atomic number material has the additional benefit of performing a weak filtering of Kα characteristic x-rays (at 58.0 and 59.3 KeV) from a tungsten target (see FIG. 7).

Other considerations may weigh in favor of the selection of a different material of construction for the x-ray spectral filter, or alternatively the provision of a small, manageable number of interchangeable spectral filters made of different materials. For example, when thin and moderate-sized patients are to undergo x-ray imaging, the contrast for steel and iodine can be increased by employing terbium (Z=65, K-edge=52.0 KeV) as the material of which the filter is made. In imaging larger patients, the signal level is commonly of greater concern, and x-rays in Region 2 (60–80 KeV) of the spectrum are useful in increasing signal level. Thus a filter material that will not attenuate these x-rays may be preferable. In this situation, gold (Z=79, K-edge=80 KeV), lead (Z=82, K-edge=88 KeV), and bismuth (Z=83, K-edge=90.5 KeV) may be preferred materials from which the filter is constructed.

There is a limited degree of flexibility in setting the boundaries for Region 2 and Region 3, shown as 60 KeV and 80 KeV, respectively, in FIG. 6, particularly based upon what imaging parameters are to be maximized. Thus, other high atomic number materials, such as lutetium, tantalum, and tungsten would be alternative preferred materials for use in constructing a spectral filter in accordance with the present invention.

In using high atomic number materials as spectral filters, there is a possibility that x-ray fluorescence will occur as x-rays above the K-edge energy of the filter material are absorbed. A secondary x-ray at a slightly lower energy may occur in such instances. Due to the low probability that such a secondary x-ray will strike the imager, the negative effect of such fluorescence is generally thought not to pose a measurable negative impact on the image, particularly for larger patients.

The effects of fluorescence can be further minimized by placing additional radiation filters adjacent to primary radiation filter material layer 1 in radiation filter 14. For example, a lead filter (Z=82) will create fluorescent x-rays primarily at 72.8 KeV and 75.0 KeV. By adding at least secondary radiation filter material layer 2 (that is, a layer of a slightly lower Z material disposed next to the lead filter such that it is disposed between the lead filter and the object to be imaged), the secondary filter material layer 2 provides preferential absorption of the x-rays resulting from the fluorescent and thus improves image quality. The material of secondary radiation filter typically has a K-edge right below the energy of the fluorescent x-rays (e.g., tungsten, Z=74, K-edge=69.5 KeV). For the range of primary filter materials discussed, the Z of the secondary radiation filter material has a value that is at least about 6 or 7 less than the Z of the primary filter material. For example, a primary filter material layer 1 material of bismuth (Z=83) should be paired with a secondary radiation filter material layer of a material having a Z less than 76; a primary filter comprising gold (Z=79) should be paired with a secondary filter having a Z less than 72; and a primary filter comprising tungsten (Z=74) should be paired with a secondary filter of a material having a Z less than 68). The thickness of the secondary filter typically has a value that is in the range between about 10% and 50% of the thickness of the primary filter. In another embodiment, additional radiation filter (e.g., a tertiary radiation filter 3) can similarly be coupled to the secondary radiation filter material layer, with the primary, secondary, and tertiary filter material layers being arranged such that the filter comprising the material with the highest Z value is disposed closest to the x-ray source and the filter comprising the material with the lowest Z value disposed farthest from the x-ray source. One example would be a filter arrangement having materials in the order of lead, tungsten, and terbium (with the lead filter being disposed closest to the radiation source).

In current x-ray imaging systems employing a 2.4 mm thick aluminum filter, it is not possible, even with heavy patients, to use available x-ray tubes at their maximum rated power (currently 900 W). With x-ray tubes having 1500 W power ratings, aluminum filters will be even more inadequate. Using a high atomic number material in constructing the spectral filter permits, as noted previously, the use of increased power, thus obtaining a better contrast-to-noise ratio and higher signal level, while at the same time keeping the dose to the patient constant. A demonstration of the improved results is presented in Table II below, and the improved results are further evidenced in FIGS. 9–11.

Table II sets forth two examples of the use of a thulium filter, for thin and medium patients, and of the use of a gold filter for heavy patients. The results for rCNR and Relative Signal reported in the table are in terms of improvement over the use of a 2.4 mm thick aluminum spectral filter (e.g. a result reported as 1.21 indicates 21% improvement over the value obtained when the 2.4 mm aluminum filter is used). It is noted that, for the thulium and gold filters are employed in these examples, the x-ray tube contained a 1.0 mm thick aluminum pre-filter. In the examples below employing thulium filters, the thickness of the thulium for a medium dose is 194 μm, and, for a low dose, is 298.5 μm. The gold filters for medium and low dose were 39.5 μm and 91 μm, respectively.

TABLE II

| Filter and Power (In addition to 1 mm Al) | Exposure to Patient | rCNR Steel | rCNR Iodine | rCNR Bone | rCNR Density | Relative Signal |
|---|---|---|---|---|---|---|
| Category 1: Thin Patient (20 cm Lucite, 75 KVp): Relative to 2.4 mm Al Spectrum | | | | | | |
| 194 μm Tm, 1500 W | 0.84 | 1.29 | 1.26 | 1.31 | 1.41 | 1.81 |
| 298.5 μm Tm, 1500 W, LD | 0.84 | 1.24 | 1.34 | 1.32 | 1.41 | 2.15 |
| Category 2: Medium Patient (24.5 cm Lucite, 90 kVP): Relative to 2.4 mm Al Spectrum | | | | | | |
| 104.5 μm Tm, 1500 W | 1.00 | 1.22 | 1.25 | 1.22 | 1.21 | 1.44 |
| 194 μm Tm, 1500 W, LD | 1.00 | 1.23 | 1.37 | 1.33 | 1.33 | 1.74 |
| Category 3: Heavy Patient (28.5 cm Lucite, 120 kVp): Relative to 2.4 mm Al Spectrum | | | | | | |
| 39.5 μm Au, 1500 W | 1.00 | 1.12 | 1.13 | 1.17 | 1.20 | 1.49 |
| 91 μm Au, 1500 W, LD | 1.00 | 1.14 | 1.16 | 1.25 | 1.31 | 1.85 |

In the case of the imaging of a thin patient (20 cm thick lucite, 75 kVp), it can be seen that, with a lower dose (0.84), the contrast-to-noise ratio (rCNR) improves by 21–31%, with an increase of about 81% in the signal level. As can be determined from the table, when it is desired to conduct a low dose fluoroimaging, the filters of the present invention make it preferable to retain the same x-ray tube current and power, and to increase the thickness of the filter itself to reduce the patient dose. This may be contrasted with the need, when conventional filter materials are employed, to reduce the x-ray tube current and power. In the case of the thin patient simulation, the rCNR value increased from 24% to 41% over the value obtained with the 2.4 mm aluminum filter, and the signal increased by 215%, while delivering only 84% of the dose delivered when the aluminum filter was used. Similar highly advantageous increases in rCNR and signal level were obtained in the medium and heavy patient simulations.

Figure 9:
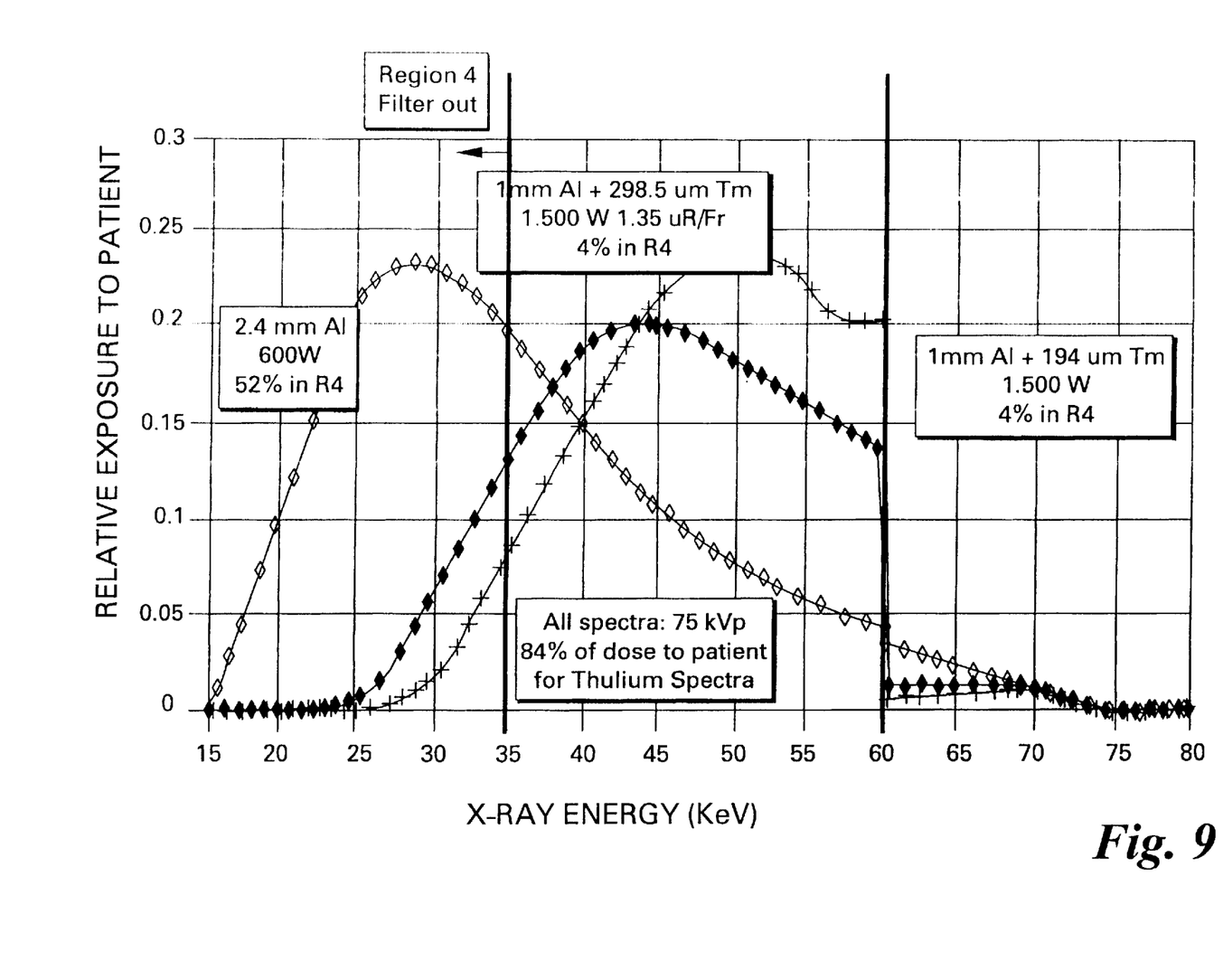
FIG. 9 is a graph illustrating the regions of x-ray energies, at a 75 kVp beam setting, that are filtered using a thulium filter, as compared with an aluminum filter.
Figure 10:
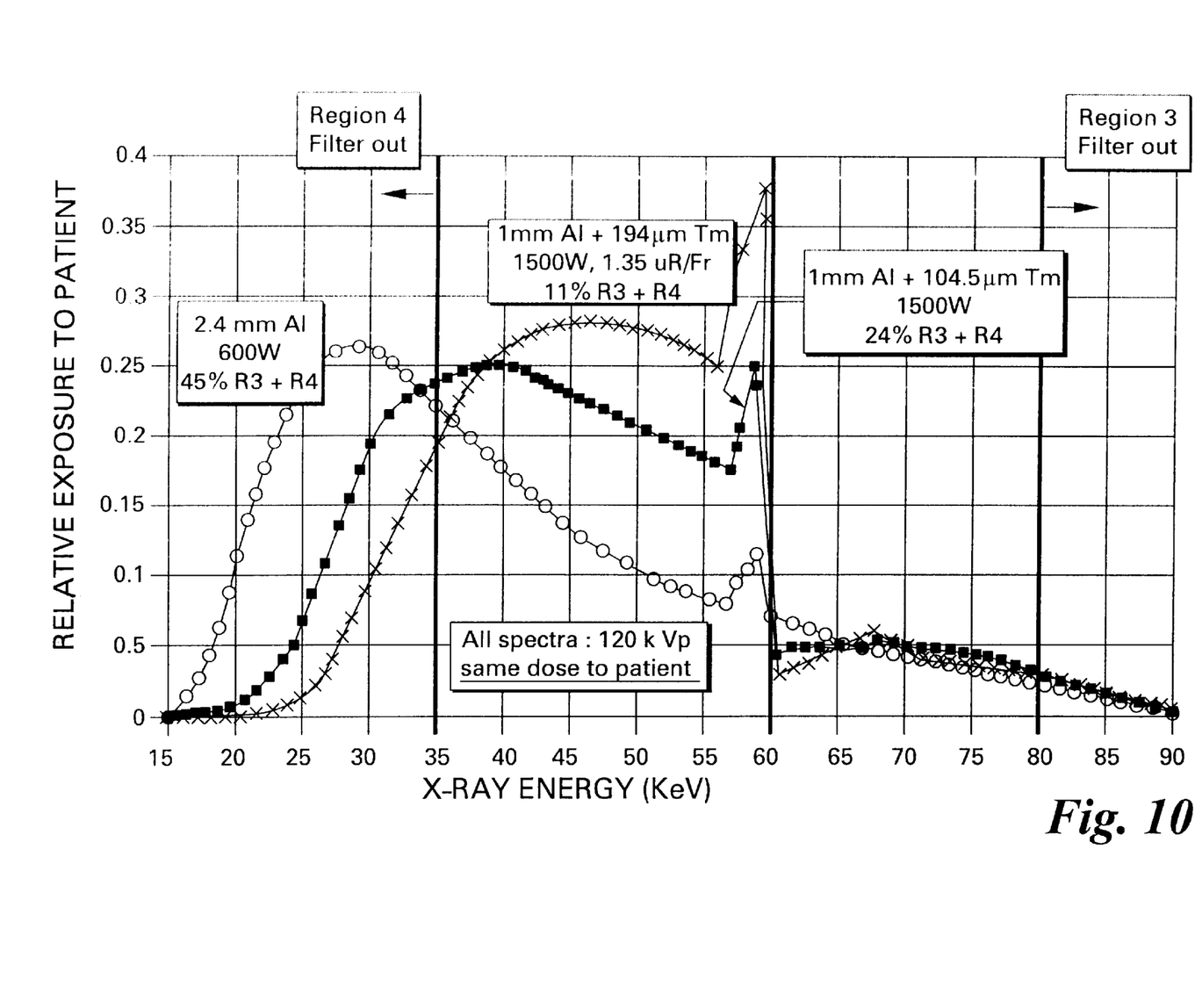
FIG. 10 is a graph illustrating the regions of x-ray energies, at a 90 kVp beam setting, that are filtered using a thulium filter, as compared with an aluminum filter.
Figure 11:
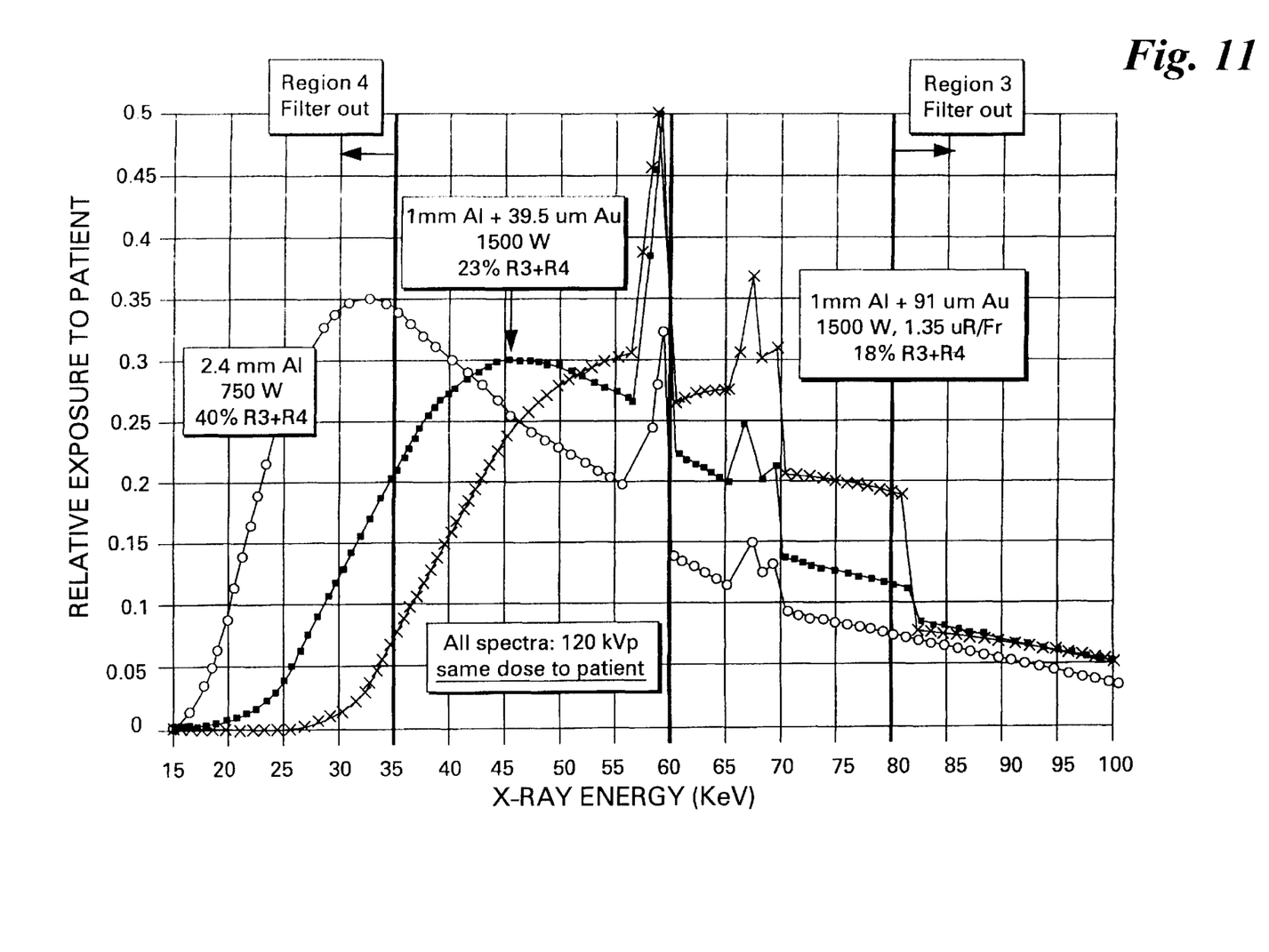
FIG. 11 is a graph illustrating the regions of x-ray energies, at a 120 kVp beam setting, that are filtered using a gold filter, as compared with an aluminum filter.

It can be inferred from the results of the simulation reported in Table II and FIGS. 9–11, that the high atomic number spectral filters may be used, instead of to improve image quality at patient dosages currently used, to decrease patient dosages while maintaining image qualities obtained using conventional filters in conventional systems.

The spectral filters of the present invention are preferably provided in the form of a thin metal foil made of the desired filter material housed within a frame or support. Alternatively the filter may preferably be provided in the form of a layer of oxide powder of the desired filter material which is encapsulated or encased in a frame structure.

The filter 14 may generally has a surface area of about one square inch (1.0 in$^2$), in order to intercept substantially all of the x-rays emanating from the x-ray tube. Copper or other relatively inexpensive, lower Z materials may alternatively be used as a pre-filter 13, in the place of aluminum. The spectral filter 14 is also preferably positioned as close as is practicable to the x-ray window, as this also permits the filter to be as small in size as possible.

The imaging system may also be provided with a plurality of radiation spectral filters 14, which are constructed of varying high Z materials and/or thicknesses selected to provide improved imaging capabilities at reduced dosages to a wide variety of patient sizes. As an example, the imaging system 10 may be provided with the set of six filters employed in the demonstration for which the results are presented in Table II above.

It should be noted that the invention has been described with reference to particular embodiments, but that the invention is not limited to these embodiments. For example, while examples have been provided with respect to digital radiation images, the invention can similarly be practiced with respect to non-digital imagers. As understood by those skilled in the art, certain of the performance indicators presented herein are independent of the type of detector used (e.g., x-ray emission and absorption information), some relate to the scintillator used (e.g., CNR), and some relate to the particular detector used (such as CF and its role in suppressing electronic noise). Those skilled in the art will understand that other modifications may be made to the embodiments discussed herein that are within the scope of the invention.

What is claimed is:

1. An imaging system comprising:
   a radiation source comprising an x-ray generator for emitting a beam of penetrating radiation toward an object to be imaged;
   a spectral radiation filter positioned between said radiation source and said object to be imaged, said spectral radiation filter being positioned in the path of said beam of penetrating radiation and being sized to intercept substantially all x-rays in said radiation beam;
   said at least one spectral radiation filter comprising a material having atomic number (Z) of at least 58, said radiation filter further being disposed to attenuate x-rays having energies at a low end and at a high end of a spectrum of x-rays emitted by said x-ray generator from passing therethrough so as to provide preferential passage of a selected intermediate spectrum of x-rays for imaging of said object; and
   a radiation detector positioned to receive the x-rays passing through said radiation filter and through said object;
   said radiation filter further comprises a plurality of filter material layers, each of said filter material layers comprising a material having a respective Z value, said filter materials being disposed such that material having a Z value higher than the Z value of another filter material are disposed closer to said radiation source, each of said filter materials having a respective Z value that differs from an adjacent layer by a value of at least 6 so as to reduce x-ray fluorescence radiation reaching said object to be imaged.

2. An imaging system as recited in claim 1, wherein said radiation filter comprises a material having an atomic number (Z) in the range of about 58 to about 83.

3. An imaging system as recited in claim 2, wherein said radiation filter comprises a material having an atomic number (Z) of at least 65.

4. An imaging system as recited in claim 2, wherein said radiation filter material is selected from the group consisting of thulium (Tm), lead (Pb), and gold (Au).

5. An imaging system as recited in claim 2, wherein said low end spectrum of x-rays has an energy less than about 35 KeV and said high end spectrum of x-rays has an energy of greater than about 80 KeV.

6. An imaging system as recited in claim 1 wherein said at least one radiation filter comprises a plurality of interchangeable radiation filters, wherein at least a first filter of said plurality of filters comprises a first selected material and having a first selected thickness for use with objects of a first size, and wherein at least a second filter of said plurality of filters comprises a second material that is different from said first selected material.

7. An imaging system as recited in claim 1 wherein said at least one radiation filter comprises a plurality of interchangeable radiation filters, wherein at least a first filter of said plurality of filters comprises a first selected material having a first selected thickness for use with objects of a first size, and wherein at least a second filter of said plurality of filters comprises said first selected material having a second selected thickness for use with objects of a second size.

* * * * *